United States Patent [19]

Ageishi et al.

[11] Patent Number: 4,986,935
[45] Date of Patent: Jan. 22, 1991

[54] WAVELENGTH CONVERTING DEVICE

[75] Inventors: Kentaro Ageishi; Lyong S. Pu, both of Kanagawa, Japan

[73] Assignee: Fuji Xerox Co., Ltd., Tokyo, Japan

[21] Appl. No.: 451,157

[22] Filed: Dec. 15, 1989

Related U.S. Application Data

[63] Continuation of Ser. No. 308,859, Feb. 9, 1989, abandoned.

[30] Foreign Application Priority Data

Feb. 10, 1988 [JP] Japan .................................. 63-27435

[51] Int. Cl.$^5$ .............................................. F21V 9/04
[52] U.S. Cl. .................................. 252/587; 252/583; 350/1.1; 350/364; 350/354
[58] Field of Search ............... 252/583, 587, 588, 589; 350/1.1; 558/411, 414; 568/306, 308, 326, 328, 381, 715, 839

[56] References Cited

U.S. PATENT DOCUMENTS

| | | |
|---|---|---|
| 3,617,270 | 11/1971 | Kampfer .............................. 96/1.7 |
| 4,199,698 | 4/1980 | Bethea et al. ........................ 307/425 |
| 4,376,899 | 3/1983 | Chemla et al. ....................... 307/425 |

FOREIGN PATENT DOCUMENTS

| | | | |
|---|---|---|---|
| 62-249951 | 10/1987 | Japan | 558/411 |
| 62-249952 | 10/1987 | Japan | 558/411 |

Primary Examiner—John S. Maples
Assistant Examiner—Richard Treanor
Attorney, Agent, or Firm—Finnegan, Henderson, Farabow, Garrett and Dunner

[57] ABSTRACT

A wavelength converting device exhibiting high activity for SHG is disclosed, which comprises a compound represented by formula (I)

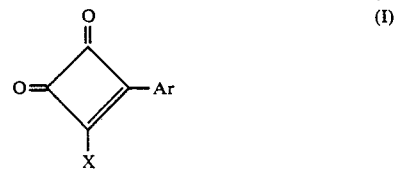

where Ar represents the residue of a $\pi$-electron conjugated molecule; and X represents a hydroxyl group, an alkoxy group, or a halogen atom.

7 Claims, 1 Drawing Sheet

WAVELENGTH CONVERTING DEVICE

This is a continuation of application Ser. No. 07/308,859, filed Feb. 9, 1989, now abandoned.

FIELD OF THE INVENTION

The present invention relates to a nonlinear optical device, in particular, a wavelength converting device that contains molecules of a conjugated π-electron system having a cyclobutenedione ring.

BACKGROUND OF THE INVENTION

Materials for nonlinear optical devices are used extensively as wavelength converting devices, optical shutters, and the like in laser transmitters and the like. Materials for nonlinear optical devices known today include crystals of inorganic substances such as KDP $KH_2PO_4$) and lithium niobate ($LiNbO_3$) and those of organic substances such as 2-methyl-4-nitroaniline (MNA). It is generally known that compared to inorganic crystals, organic crystals are about 10 to 100 times larger in the coefficient of second harmonic wave generation (hereinafter abbreviated as SHG), about 1000 times faster in optical response and have higher thresholds for optical damage.

SHG does not occur in single crystals having a center of symmetry. Among crystalline organic substances known today, MNA which assumes a crystal form having no center of symmetry is active for SHG and the intensity of its SHG is about 20 times as great as urea. However, MNA has a low melting point and is incapable of phase matching in crystal form. A strong need has, therefore, arisen for the development of an organic material for nonlinear optical devices which is stable and capable of readily producing a large single crystal that has no center of symmetry and which exhibits high activity for SHG.

SUMMARY OF THE INVENTION

The present invention is directed to such an organic material referred to above. The primary object, therefore, of the present invention is to provide an organic material for wavelength converting devices that is stable at room temperature and is capable of readily producing a large single crystal having high activity for SHG owing to the absence of a center of symmetry.

This object of the present invention can be attained by a material for wavelength converting devices which has a 1,2-cyclobutenedione ring as an electronwithdrawing substituent, as represented by formula (I)

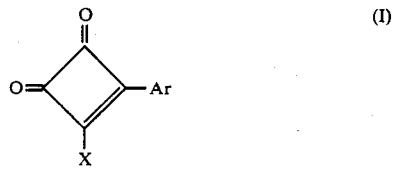

(I)

where Ar represents the residue of a compound of a πelectron conjugated molecule; and X represents a hydroxyl group, an alkoxy group or a halogen atom.

DETAILED DESCRIPTION OF THE INVENTION

Figure 1:
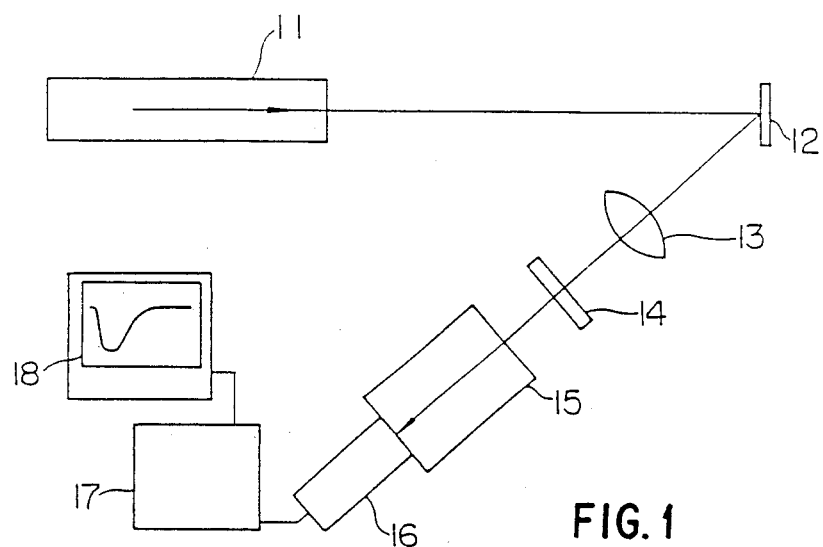
FIG. 1 is a block diagram of an optical system for use in evaluating the intensity of SHG by the powder method.

In formula (I) which represents the compound used in the wavelength converting device of the present invention, Ar denotes the residue of a compound of a π-electron conjugated molecule, and examples of Ar include monovalent groups obtained by removal of one hydrogen atom from aromatic, polycycloaromatic or heterocyclic compounds. The term "π-electron conjugated molecule" includes benzene, naphthalene, anthracene, pyridine, stilbene, azobenzene, diphenylacetylene and diphenyldiacetylene. X represents a hydroxyl group, an alkoxy group preferably having 1 to 20 carbon atoms and more preferably 1 to 10 carbon atoms, or a halogen atom (Cl, Br, F and I).

Preferred examples of the compound of formula (I) are those having an electron-donating group and/or an electron-accepting group as a substituent, and particularly preferred are those having a dimethylaminophenyl group. Illustrative electron-donating groups include amino, dimethylamino, methoxy, ethoxy, hydroxyl groups, and the like, and illustrative electron-accepting group include nitro, cyano, aldehyde, carboxyl groups, and the like.

Specific examples of the compounds of formula (I) include: arylalkoxycyclobutenediones such as 4-phenyl-3-ethoxycyclobutenedione, 4-(4'-dimethylaminophenyl)-3-ethoxycyclobutenedione, 4-(4'-dimethylamino2'-fluorophenyl)-3-ethoxycyclobutenedione, 4-(4'-dimethylamino-2'-methylphenyl)-3-ethoxycyclobutenedione, 4-(4'-dimethylamino-2',6'-dihydroxyphenyl)-3-ethoxycyclobutenedione, 4-(4'-methoxyphenyl)-3-ethoxycyclobutenedione, 4-phenyl-3-methoxycyclobutenedione and 4-phenyl-3-butoxycyclobutenedione; arylhalocyclobutenediones such as 4-phenyl-3-chlorocyclobutenedione, 4-(4'-dimethylaminophenyl)-3-chlorocyclobutenedione, 4-(4'-dimethylamino-2'-fluorophenyl)-3-chlorocyclobutenedione, 4-(4'-dimethylamino-2,-methylphenyl)-3-chlorocyclobutenedione, 4-(4'-dimethylamino-2',6'-dihydroxyphenyl).3-chlorocyclobutenedione, 4-(4'-methoxyphenyl)-3-chlorocyclobutenedione, 4-phenyl-3-bromocyclobutenedione, 4-phenyl-3-iodocyclobutenedione and 4-phenyl-3-fluorocyclobutenedione; and arylhydroxycyclobutenediones such as 4-phenyl-3-hydroxycyclobutenedione, 4-(4'-dimethylaminophenyl)-3-hydroxycyclobutenedione, 4-(4'-dimethylamino-2'-fluorophenyl)-3-hydroxycyclobutenedione, 4-(4'-dimethylamino-2'-methylphenyl)-3-hydroxycyclobutenedione, 4-(4'-dimethylamino-2',6'-dihydroxyphenyl)-3-hydroxycyclobutenedione and 4-(4'-methoxyphenyl)-3-hydroxycyclobutenedione.

The above compounds can be synthesized by either reaction (A) or reaction (B) which are shown below:

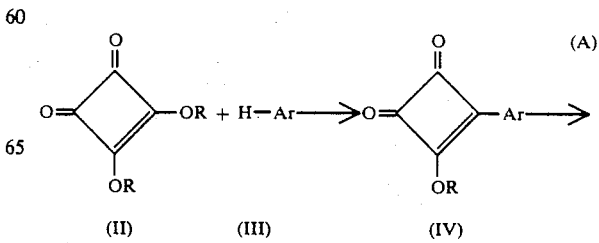

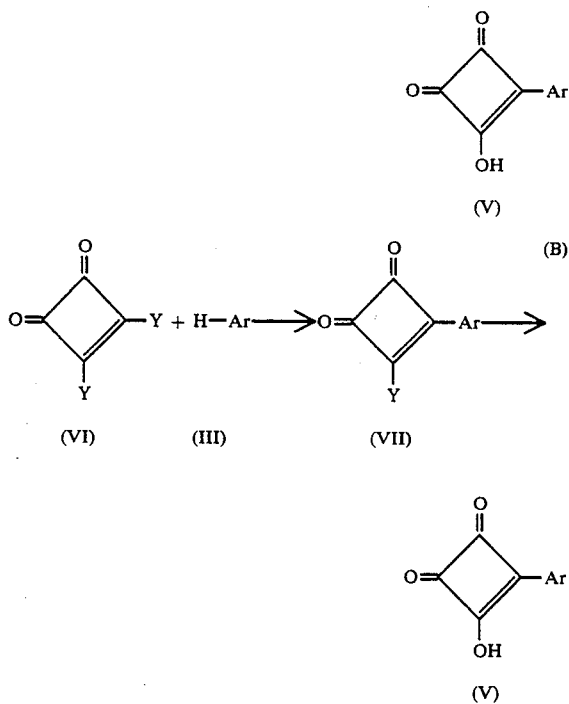

where R is an alkyl group preferably having 1 to 20 carbon atoms and more preferably 1 to 10 carbon atoms, Y is a halogen atom (Cl, Br, F or I), and Ar has the same meaning as defined for formula (I).

An example of reaction (A) is described as follows: about 20 to 100 mmol of a dialkyl squalate of the above formula (II) is reacted with about 20 to 200 mmol of a compound of the above formula (III), e.g., 3-nitrodimethylaniline at room temperature (10° to 30° C.) in the presence of about 50 to 200 mmol of a trialkyl oxonium salt such as triethyl oxonium fluoroborate (catalyst), and about 50 to 250 mmol of a halogenation solvent such as methyl chloride; after stirring for 6 to 12 hours, the solvent is distilled off under vacum to obtain an alkoxycyclobutenedione derivative of the above formula (IV); this derivative is hydrolyzed by heating in a 2 to 5% aqueous solution of sulfuric acid for about 1 to 8 hours at a temperature of about 50° to 80° C. to produce a monosubstituted squaline compound of the above formula (V) in a yield of about 10 to 30%.

An example of reaction (B) is described as follows: about 20 to 50 mmol of a compound of the above formula (III), e.g., 3-hydroxydimethylaniline is reacted with about 60 to 150 mmol of dichlorocyclobutenedione of the above formula (VI) by heating under reflux in about 100 to 1000 ml of a Friedel-Crafts solvent (e.g., carbon disulfide, nitrobenzene or methylene chloride). This reaction is performed in the presence of a catalyst, preferably about 200 to 900 mmol of aluminum chloride or cuprous chloride. After continuing the reaction for about 4 to 8 hours, the Freidel-Crafts solvent is removed to obtain a chlorocyclobutenedione derivative of the above formula (VII); this derivative is hydrolyzed by heating in a 60 to 80% solution of sulfuric acid for about 1 to 8 hours at a temperature of about 50° to 80° C. to obtain a monosubstituted squaline compound of the above formula (V) in a yield of about 10 to 30%.

The compound of formula (I) has a high boiling point and is thermally more stable than MNA (m.p. 131° to 133° C.). The hydrolyzate of this compound has a hydroxyl group, and because of the presence of this hydrogen binding substituent, inversion symmetry is suppressed to produce a single crystal having no center of symmetry. These compounds have high activity for SHG. For instance, when they are illuminated in powder form with a light from a Nd:YAG (yttrium aluminum garnet) laser (wavelength, 1,064 nm; output, 189 mJ/pulse), these compounds emit green light at a wavelength of 532 nm (half the wavelength of incident light) with a high intensity of SHG, thereby producing excellent nonlinear optical effects, particularly suitable for wavelength converting devices which make it possible to use a photoreceptor having light-sensitivity to visible light in an exposure system using laser beam of a longer wavelength.

The compound of the present invention is used in the crystalline state and may be used in a wavelength converting device as it is or in the form of layer provided on a substrate. For example, a fine crystalline powder of the compound is charged in a glass cell which is placed on the light path, or a single crystal of the compound is placed on the light path, the latter being preferred because higher SHG efficiency is realized. There are known various methods for producing a single crystal such as a solution method wherein a single crystal is precipitated using a poor solvent, a hot-melting method wherein a compound is melted and then solidified, a recrystallization method generally applied for production of single crystal of metal, a flux method utilizing the phenomenon of decrease in melting point by addition of a flux, a method using vapor deposition or electrolytic deposition and the like. These methods are described in detail in, for example, "Jikken Kagaku Koza -Kotar Butsuri Kagaku" (Lecture in Experimental Chemistry - Solid Physical Chemistry), vol. 4, pp. 1–32, published by Maruzen (May 25, 1966), JP-A-62-207792, "Journal of Chemical Physics", vol. 66, No. 8, p. 3806 (1977).

Semiconductor laser such as (GaAl)As double heterojunction diode laser as well as YAG laser can be used as a light source for the wavelength conversion in accordance with the present invention.

The compound of formula (I) prepared in accordance with the present invention is also useful in nonlinear optical devices, other than wavelength converting devices, such as light shutters, high-speed light switching devices, optical logic gates, phototransistors, optical fibers as a core material, and the like.

The following examples are provided for the purpose of further illustrating the present invention, but are not to be taken as limiting.

EXAMPLE 1

Diethyl squalate (8.5 g, 50 mmol) was added to 100 ml of a methylene chloride solution containing 19 g (100 mmol) of triethyl oxonium tetrafluoroborate and thereafter, 50 ml of a methylene chloride solution containing 6.1 g (50 mmol) of N-dimethylaniline was added in a nitrogen stream over a period of about 1 hour, followed by stirring at room temperature for 6 hours. Subsequently, the reaction mixture was washed with distilled water and the methylene chloride phase was concentrated and recrystallized with ethanol to give 4-(4'-dimethylaminophenyl)-3 ethoxycyclobutenedione. Elemental analysis for $C_{14}H_{15}N_1O_3$:

Found: C, 68 21%; H, 6.04%; N, 5.63%

Cal'd: C, 68.55%; H, 6.17%; N, 5.71% m.p. $\geq$ 300° C.; $\lambda max = 394$ nm.

Two grams of the compound described above was added to a mixture of distilled water (50 ml) and concentrated sulfuric acid (2 ml), and the resulting solution was hydrolyzed at 70° C. for 5 hours. The solution was then cooled showly to obtain 1 g of a yellow needle-like substance. The obtained compound, 4-(4'-dimethylaminophenyl)-3-hydroxycyclobutenedione, had a melting point of 209° C. and the results of its elemental analysis for $C_{12}H_{11}N_1O_3$ were as follows:

Found: C, 66.26%; H, 4.98%; N, 6.42%
Cal'd: C, 66.35%; H, 5.11%; N, 6.45% λmax=375 nm.

A glass cell packed with 4-(4'-dimethylaminophenyl)-3-ethoxycyclobutenedione and 4-(4'-dimethylaminophenyl)-3-hydroxycyclobutenedione in powder form was irradiated with Nd:YAG laser light (wavelength, 1.064 nm; output, 180 mJ/pulse), green scattered light having a wavelength of 532 nm was emitted due to SHG. The intensity of this light was about 3 times as great as that produced from urea.

FIG. 1 is a block diagram of the optical system used to evaluate the intensity of SHG by the powder method described above. In FIG., 1, 11 denotes the Nd:YAG laser; 12, the powder sample packed in the glass cell; 13, a lens; 14, a filter; 15, a monochromator; 16, a photomultiplier tube; 17 a boxcar integrator;; and 18, an oscilloscope. The Sample 12 was irradiated with light (λ, 1,064 nm) from the Nd:YAG laser 11 and the intensity of SHG was determined by measuring the emitted green scattered light (λ, 532 nm) with the aid of the photomultiplier tube 6.

EXAMPLE 2

2-Methyl-N,N-dimethyltoluidine (2.3 g, 50 mmol) and dichlorocyclobutenedione (7.5 g, 50 mmol) were mixed with 125 ml of carbon disulfide. To the mixture, 20 g of aluminum chloride was added, followed by heating for 6 hours under reflux. After removing the carbon disulfide, 250 ml of ice water was added to the residue. The resulting 4-(4'-dimethylamino-2'-methylphenyl)-3-chlorocyclobutenedione was recrystallized from ethanolacetone.

Elemental analysis for $C_{16}H_{17}N_1O_4.1/2H_2O_2O$:
Found: C, 60.31%; H, 5.25%; N, 5.25%
Cal'd: C, 60.34%; H, 5.03%; N, 5.41% m.p. ≧ 300° C.

Two grams of the compound described above was added to a mixture of distilled water (3 ml) and glacial acetic acid (30 ml), and the resulting solution was hydrolyzed at 70° C. for 3 hours to obtain 4-(4'-dimethylamino-2'-methylphenyl) -3-hydroxycyclobutenedione. An elemental analysis of this compound in fine crystalline powder form gave the following results:

Elemental analysis for $C_{13}H_{13}N_1O_3.1/2H_2O$:
Found: C, 64.97%; H, 5.44%; N, 5.75%
Cal'd: C, 64.93%; H, 5.83%; N, 5.83% m.p.≧114° C.

Sample powders of 4-(4'-dimethylamino-2'-methylphenyl) -3-chlorocyclobutenedione and 4-(4'-dimethylamino-2'-methylphenyl)-3-hydroxycyclobutenedione were treated as in Example 1 to demonstrate their activity for SHG, which was found to be about 5 times as high as that of urea.

EXAMPLE 3

Diethyl squalate (8.5 g, 5 mmol) was added to 100 ml of a methylene chloride solution containing 19 g (100 mmol) of triethyloxonium tetrafluoroborate. Thereafter, 50 ml of a methylene chloride solution containing 6.8 g (50 mmol) of 3-hydroxy-N,N-dimethylaniline was added in a nitrogen stream over a period of about 1 hour and the mixture was stirred for about 6 hours at room temperature. The stirred mixture was washed with distilled water and the methylene chloride phase was concentrated and recrystallized from ethanol to produce 4-(3'-hydroxy-4'-dimethylaminophenyl)-3-ethoxycyclobutenedione as a yellow needle-like substance.

Elemental analysis for $C_{14}H_{15}N_1O_4$:
Found: C, 64.16%; H, 5.59%; N, 5.27%
Cal'd: C, 64.35%; H, 5.79%; N, 5.36% m.p. ≧ 182° C.; λmax=399 nm.

Two grams of the compound described above was added to a mixture of distilled water (50 ml) and conc. sulfuric acid (2 ml) and the resulting solution was hydrolyzed at 70° C. for 5 hours. The solution was then cooled slowly to obtain 0.8 g of a brown powder. The obtained compound 4-(3'-hydroxy-4'-dimethylaminophenyl)-3-hydroxycyclobutenedione, was subjected to elemental analysis for $C_{12}H_{11}N_1O_4$, giving the following results:

Found: C, 62.03%; H, 4.43%; N, 5.90%
Cal'd: C, 61.80%; H, 4.75%; N, 6.01% m.p. 297° C.

Sample powders of 4-(3'-hydroxy-4'-dimethyl-aminophenyl)-3-ethoxycyclobutenedione and 4-(3'-hydroxy4'-dimethylaminophenyl)-3-hydroxycyclobutenedione were treated as in Example 1 to determine their activity for SHG, which was found to be about 3 times as high as that of urea.

EXAMPLES 4 TO 6

Repeating the procedures of Example 3, except that the 3-hydroxy-N,N-dimethylaniline was replaced by other aniline derivatives, the following corresponding compounds were synthesized; 4-(3'-methoxy-4'-dimethylaminophenyl)-3-hydroxycyclobutenedione (Example 4); 4-(3'-methyl-4'-dimethylaminophenyl) -3-hydroxycyclobutenedione (Example 5); and 4-(3'-nitro-4'-dimethylaminophenyl) -3-hydroxycyclobutenedione (Example 6).

The results of elemental analyses conducted on the compounds synthesized in Examples 4 to 6 are shown in the following Table 1.

TABLE 1

| Example | Molecular formula | Found | Cal'd |
|---|---|---|---|
| 4 | $C_{13}H_{13}N_1O_4$ | C, 62.97 | C, 63.15 |
|  |  | H, 5.2 | H, 5.30 |
|  |  | N, 5.59 | N, 5.67 |
|  | m.p. 242° C. | λmax = 377 nm |  |
| 5 | $C_{13}H_{13}N_1O_3$ | C, 67.20 | C, 67.52 |
|  |  | H, 5.45 | H, 5.67 |
|  |  | N, 5.70 | N, 6.06 |
|  | m.p. 306° C. | λmax = 364 nm |  |
| 6 | $C_{12}H_{10}N_2O_5$ | C, 54.51 | C, 54.96 |
|  |  | H, 3.64 | H, 3.84 |
|  |  | N, 10.20 | N, 10.69 |
|  | m.p. 217° C. |  |  |

Samples of these compounds in powder form were packed in a glass cell and irradiated with light having a wavelength of 1,064 nm from a Nd:YAG laser as in Example 1 and the emitted green light having a wavelength of 532 nm was observed. The results are shown in the following Table 2.

TABLE 2

| Example | Intensity of SHG* |
|---|---|
| 4 | 2.5 |
| 5 | 6.0 |
| 6 | 4.0 |

*Relative intensity, with the value for urea being taken as unity.

EXAMPLE 7

Figure 2:
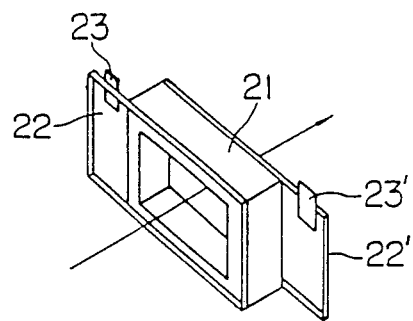
FIG. 2 is a perspective view of the solution cell used in Example 7 in measuring the SHG intensity of material of the present invention.

A saturated solution in 1,4-dioxane of the 4-(3'-hydroxy-4'-dimethylaminophenyl) -3-ethoxycyclobutenedione prepared in Example 3 was placed in a solution cell of the type shown in FIG. 2 and subjected to an SHG intensity measurement. FIG. 2 is a perspective view of the solution cell composed of a solution holder 21 that was sandwiched between two transparent electroconductive glass plates 22 and 22' (coated with either a tin oxide or an indium-tin oxide) and to which were attached electrodes 23 and 23'. The SHG intensity measurement was performed by the following method: a DC static electric field of 5 kV was applied to the sample solution via the conductive plates, and with the solution cell being illuminated under a Nd:YAG laser, emission of green light was observed as the second harmonic wave generation (dc SHG) of the field-induced light. It was established that the intensity of SHG was about 5 times as high as the value obtained with urea.

As will be understood from the foregoing explanation, the material for nonlinear optical devices of the present invention has a very strong SHG intensity and is sufficiently stable at room temperature to easily produce a large single crystal which exhibits excellent nonlinear optical effects. Because of the absence of a center of symmetry, this single crystal has great activity for SHG. Therefore, the material of the present invention is very suitable for use in a wavelength converting device.

Having described embodiments of the present invention it is to be understood that variations and modifications thereof falling within the spirit and scope of the invention may become apparent to those skilled in the art, and the scope of the invention is defined by the appended claims and their equivalents.

What is claimed is:

1. In a device for converting the wavelength of light emitted by a light source to a second wavelength comprising a light source for emitting light and an organic compound disposed in the path of the emitted light the improvement wherein said organic compound is a II-electron conjugated compound having a 1,2-cyclobutenedione ring as an electron-withdrawing substituent and being represented by formula (I)

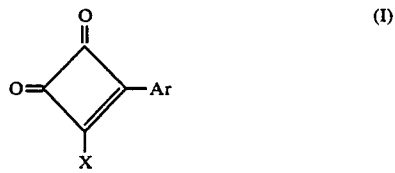

where Ar represents the residue of a $\pi$-electron conjugated molecule; and X represents a hydroxyl group, an alkoxy group, or a halogen atom, said II-electron conjugated compound being capable of reducing the wavelength of the emitted laser light to a second wavelength utilizing second harmonic wave generation.

2. The device of claim 1, wherein said II-electron conjugated molecule is a monovalent group obtained by removal of one hydrogen from a single ring aromatic, polycyclic aromatic or heterocyclic compound.

3. The device of claim 1, wherein said $\pi$-electron conjugated molecule has electron-donating group and/or an electron-accepting group as a substituent.

4. The device of claim 3, wherein said $\pi$-electron conjugated molecule is selected from the group consisting of benzene, naphthalene, anthracene, pyridine, stilbene, azobenzene, diphenylacetylene and diphenyldiacetylene; said electron-donating group is selected from the group consisting of amino, dimethylamino, methoxy, ethoxy and hydroxyl groups; and said electron-accepting group is selected from the group consisting of nitro, cyano, aldehyde and carboxyl groups.

5. The device of claim 1, wherein said compound is an arylalkoxylcyclobutenedione, an arylhalocyclobutenedione, or an arylhydroxycyclobutenedione.

6. The device of claim 1, wherein said light source is a laser.

7. The device of claim 1, wherein said compound is in crystalline form.

* * * * *